United States Patent
Jaffe et al.

(10) Patent No.: US 8,389,957 B2
(45) Date of Patent: Mar. 5, 2013

(54) SYSTEM AND METHOD FOR METERED DOSAGE ILLUMINATION IN A BIOANALYSIS OR OTHER SYSTEM

(75) Inventors: Claudia B. Jaffe, Portland, OR (US);
Steven M. Jaffe, Portland, OR (US);
David Larsen, Beaverton, OR (US)

(73) Assignee: Lumencor, Inc., Beaverton, OR (US)

( * ) Notice: Subject to any disclaimer, the term of this patent is extended or adjusted under 35 U.S.C. 154(b) by 314 days.

(21) Appl. No.: 13/007,535

(22) Filed: Jan. 14, 2011

(65) Prior Publication Data

US 2012/0181936 A1  Jul. 19, 2012

(51) Int. Cl.
| | |
|---|---|
| F21V 9/16 | (2006.01) |
| G01J 1/58 | (2006.01) |
| G01T 1/10 | (2006.01) |
| G21H 3/02 | (2006.01) |
| G21K 5/00 | (2006.01) |
| H01J 65/06 | (2006.01) |
| H01J 65/08 | (2006.01) |
| H05B 37/02 | (2006.01) |
| H05B 39/04 | (2006.01) |
| H01J 3/14 | (2006.01) |
| H01J 5/16 | (2006.01) |
| G01N 21/85 | (2006.01) |

(52) U.S. Cl. .................. 250/458.1; 250/216; 315/151; 356/417

(58) Field of Classification Search ................ None
See application file for complete search history.

(56) References Cited

U.S. PATENT DOCUMENTS

| | | | |
|---|---|---|---|
| 1,998,054 A | 4/1935 | McBurney | |
| 3,313,337 A | 4/1967 | Bernat | |
| 3,637,285 A | 1/1972 | Stewart | |
| 3,759,604 A | 9/1973 | Thelen | |
| 3,881,800 A | 5/1975 | Friesem | |
| 3,982,151 A | 9/1976 | Ludovici | |
| 4,003,080 A | 1/1977 | Maiman | |

(Continued)

FOREIGN PATENT DOCUMENTS

| | | |
|---|---|---|
| CA | 2 280 398 | 4/2000 |
| EP | 1 426 807 | 12/2003 |

(Continued)

OTHER PUBLICATIONS

Deck, L., et al., "Two color light-emitting-diode source for high precision phase-shifting interferometry", Optics Letters, vol. 18, No. 22, Nov. 15, 1993, pp. 1899-1901.

(Continued)

*Primary Examiner* — Douglas W Owens
*Assistant Examiner* — Dedei K Hammond
(74) *Attorney, Agent, or Firm* — Fliesler Meyer LLP (57) ABSTRACT

A system and method for metered dosage illumination in a bioanalysis or other system. In accordance with an embodiment, an illumination system or subsystem is described that can provide optimized amounts of excitation light within the short exposure times necessary to measure fast biological activity. The amount of light can be precisely measured to provide quantitative results. The light flux can also be precisely controlled to generate only a prescribed minimum amount of light, in order to reduce adverse lighting effects on both fluors and samples. Although the examples herein illustrate the providing of metered dosage illumination in the context of a bioanalysis system, the techniques can be similarly used to provide metered dosage illumination in the context of other types of system.

9 Claims, 5 Drawing Sheets

U.S. PATENT DOCUMENTS

| | | |
|---|---|---|
| 4,298,820 A | 11/1981 | Bongers |
| 4,371,897 A | 2/1983 | Kramer |
| 4,510,555 A | 4/1985 | Mori |
| 4,539,687 A | 9/1985 | Gordon |
| 4,626,068 A | 12/1986 | Caldwell |
| 4,642,695 A | 2/1987 | Iwasaki |
| 4,644,141 A | 2/1987 | Hagen |
| 4,695,332 A | 9/1987 | Gordon |
| 4,695,732 A | 9/1987 | Ward |
| 4,695,762 A | 9/1987 | Berkstresser |
| 4,713,577 A | 12/1987 | Gualtieri |
| 4,724,356 A | 2/1988 | Daehler |
| 4,798,994 A | 1/1989 | Rijpers |
| 4,804,850 A | 2/1989 | Norrish et al. |
| 4,852,985 A | 8/1989 | Fujihara et al. |
| 4,937,661 A | 6/1990 | Van der Voort |
| 4,995,043 A | 2/1991 | Kuwata |
| 5,052,016 A | 9/1991 | Mahbobzadeh |
| 5,089,860 A | 2/1992 | Deppe |
| 5,109,463 A | 4/1992 | Lee |
| 5,126,626 A | 6/1992 | Iwasaki |
| 5,128,846 A | 7/1992 | Mills et al. |
| 5,137,598 A | 8/1992 | Thomas |
| 5,193,015 A | 3/1993 | Shanks |
| 5,200,861 A | 4/1993 | Moskovich |
| 5,226,053 A | 7/1993 | Cho |
| 5,231,533 A | 7/1993 | Gonokami |
| 5,233,372 A | 8/1993 | Matsumoto |
| 5,249,195 A | 9/1993 | Feldman |
| 5,285,131 A | 2/1994 | Muller |
| 5,289,018 A | 2/1994 | Okuda |
| 5,312,535 A | 5/1994 | Waska |
| 5,315,128 A | 5/1994 | Hunt |
| 5,332,892 A | 7/1994 | Li et al. |
| 5,345,333 A | 9/1994 | Greenberg |
| 5,363,398 A | 11/1994 | Glass |
| 5,416,342 A | 5/1995 | Edmond et al. |
| 5,416,617 A | 5/1995 | Loiseaux |
| 5,418,584 A | 5/1995 | Larson |
| 5,428,476 A | 6/1995 | Jensen |
| 5,469,018 A | 11/1995 | Jacobsen |
| 5,475,281 A | 12/1995 | Heijboer |
| 5,478,658 A | 12/1995 | Dodabalapur |
| 5,489,771 A | 2/1996 | Beach et al. |
| 5,493,177 A | 2/1996 | Muller |
| 5,500,569 A | 3/1996 | Blomberg |
| 5,542,016 A | 7/1996 | Kaschke |
| 5,616,986 A | 4/1997 | Jacobsen |
| 5,644,676 A | 7/1997 | Blomberg |
| 5,658,976 A | 8/1997 | Carpenter |
| 5,669,692 A | 9/1997 | Thorgersen |
| 5,671,050 A | 9/1997 | De Groot |
| 5,674,698 A | 10/1997 | Zarling |
| 5,690,417 A | 11/1997 | Polidor et al. |
| 5,715,083 A | 2/1998 | Takayama |
| 5,719,391 A | 2/1998 | Kain |
| 5,757,014 A | 5/1998 | Bruno |
| 5,781,338 A | 7/1998 | Kapitza |
| 5,803,579 A | 9/1998 | Turnbull et al. |
| 5,804,919 A | 9/1998 | Jacobsen |
| 5,808,759 A | 9/1998 | Okamori |
| 5,827,438 A | 10/1998 | Blomberg |
| 5,833,827 A | 11/1998 | Anazawa |
| 5,858,562 A | 1/1999 | Utsugi |
| 5,864,426 A | 1/1999 | Songer |
| 5,942,319 A | 8/1999 | Oyama |
| 5,955,839 A | 9/1999 | Jaffe |
| 5,984,861 A | 11/1999 | Crowley |
| 6,110,106 A | 8/2000 | MacKinnon et al. |
| 6,154,282 A | 11/2000 | Lilge et al. |
| 6,198,211 B1 | 3/2001 | Jaffe |
| 6,204,971 B1 | 3/2001 | Morris |
| 6,222,673 B1 | 4/2001 | Austin |
| 6,293,911 B1 | 9/2001 | Imaizumi et al. |
| 6,299,338 B1 | 10/2001 | Levinson |
| 6,304,584 B1 | 10/2001 | Krupke |
| 6,366,383 B1 | 4/2002 | Roeder |
| 6,392,341 B2 | 5/2002 | Jacobsen |
| 6,404,127 B2 | 6/2002 | Jacobsen |
| 6,404,495 B1 | 6/2002 | Melman |
| 6,422,994 B1 | 7/2002 | Kaneko et al. |
| 6,444,476 B1 | 9/2002 | Morgan |
| 6,513,962 B1 | 2/2003 | Mayshack et al. |
| 6,517,213 B1 | 2/2003 | Fujita et al. |
| 6,529,322 B1 | 3/2003 | Jones |
| 6,542,231 B1 | 4/2003 | Garrett |
| 6,544,734 B1 | 4/2003 | Briscoe |
| 6,594,075 B1 | 7/2003 | Kanao et al. |
| 6,608,332 B2 | 8/2003 | Shimizu et al. |
| 6,614,161 B1 | 9/2003 | Jacobsen |
| 6,614,179 B1 | 9/2003 | Shimizu et al. |
| 6,637,905 B1 | 10/2003 | Ng |
| 6,642,652 B2 | 11/2003 | Collins |
| 6,649,432 B1 | 11/2003 | Eilers |
| 6,674,575 B1 | 1/2004 | Tandler et al. |
| 6,680,569 B2 | 1/2004 | Mueller-Mach et al. |
| 6,685,341 B2 | 2/2004 | Ouderkirk et al. |
| 6,690,467 B1 | 2/2004 | Reel |
| 6,717,353 B1 | 4/2004 | Mueller |
| 6,747,710 B2 | 6/2004 | Hall |
| 6,791,259 B1 | 9/2004 | Stokes et al. |
| 6,791,629 B2 | 9/2004 | Moskovich |
| 6,795,239 B2 | 9/2004 | Tandler |
| 6,843,590 B2 | 1/2005 | Jones |
| 6,869,206 B2 | 3/2005 | Zimmerman et al. |
| 6,870,165 B2 | 3/2005 | Amirkhanian |
| 6,926,848 B2 | 8/2005 | Le Mercier |
| 6,958,245 B2 | 10/2005 | Seul et al. |
| 6,960,872 B2 | 11/2005 | Beeson et al. |
| 6,981,970 B2 | 1/2006 | Karni |
| 6,991,358 B2 | 1/2006 | Kokogawa |
| 6,995,355 B2 | 2/2006 | Rains, Jr. et al. |
| 7,009,211 B2 | 3/2006 | Eilers |
| 7,011,421 B2 | 3/2006 | Hulse et al. |
| 7,035,017 B2 | 4/2006 | Tadic-Galeb |
| 7,083,610 B1 | 8/2006 | Murray et al. |
| 7,153,015 B2 | 12/2006 | Brukilacchio |
| 7,192,161 B1 | 3/2007 | Cleaver et al. |
| 7,205,048 B2 | 4/2007 | Naasani |
| 7,208,007 B2 | 4/2007 | Nightingale et al. |
| 7,211,833 B2 | 5/2007 | Slater, Jr. et al. |
| 7,239,449 B2 | 7/2007 | Leitel et al. |
| 7,300,175 B2 | 11/2007 | Brukilacchio |
| 7,316,497 B2 | 1/2008 | Rutherford et al. |
| 7,384,797 B1 | 6/2008 | Blair |
| 7,416,313 B2 | 8/2008 | Westphal et al. |
| 7,422,356 B2 | 9/2008 | Hama et al. |
| 7,427,146 B2 | 9/2008 | Conner |
| 7,445,340 B2 | 11/2008 | Conner |
| 7,467,885 B2 | 12/2008 | Grotsch et al. |
| 7,488,088 B2 | 2/2009 | Brukilacchio |
| 7,488,101 B2 | 2/2009 | Brukilacchio |
| 7,498,734 B2 | 3/2009 | Suehiro et al. |
| 7,540,616 B2 | 6/2009 | Conner |
| 7,633,093 B2 | 12/2009 | Blonder et al. |
| 7,709,811 B2 | 5/2010 | Conner |
| 7,746,560 B2 | 6/2010 | Yamazaki |
| 7,832,878 B2 | 11/2010 | Brukilacchio |
| 7,837,348 B2 | 11/2010 | Narendran et al. |
| 7,854,514 B2 | 12/2010 | Conner |
| 7,857,457 B2 | 12/2010 | Rutherford et al. |
| 8,029,142 B2 | 10/2011 | Conner |
| 2001/0055208 A1 | 12/2001 | Kimura |
| 2002/0109844 A1 | 8/2002 | Christel et al. |
| 2002/0127224 A1 | 9/2002 | Chen |
| 2003/0044160 A1 | 3/2003 | Jones et al. |
| 2003/0095401 A1 | 5/2003 | Hanson et al. |
| 2003/0127609 A1 | 7/2003 | El-Hage |
| 2003/0160151 A1 | 8/2003 | Zarate |
| 2003/0230728 A1 | 12/2003 | Dai |
| 2003/0233138 A1 | 12/2003 | Spooner |
| 2004/0090600 A1 | 5/2004 | Blei |
| 2004/0247861 A1 | 12/2004 | Naasani |
| 2005/0062404 A1 | 3/2005 | Jones et al. |
| 2005/0116635 A1 | 6/2005 | Walson et al. |
| 2005/0146652 A1 | 7/2005 | Yokoyama et al. |
| 2005/0152029 A1 | 7/2005 | Endo |

| | | | |
|---|---|---|---|
| 2005/0184651 | A1 | 8/2005 | Cheng |
| 2005/0201899 | A1 | 9/2005 | Weisbuch |
| 2005/0248839 | A1 | 11/2005 | Yamaguchi |
| 2005/0260676 | A1 | 11/2005 | Chandler |
| 2005/0263679 | A1 | 12/2005 | Fan |
| 2006/0002131 | A1 | 1/2006 | Schultz et al. |
| 2006/0030026 | A1 | 2/2006 | Garcia |
| 2006/0060872 | A1 | 3/2006 | Edmond |
| 2006/0060879 | A1 | 3/2006 | Edmond |
| 2006/0114960 | A1 | 6/2006 | Snee |
| 2006/0170931 | A1 | 8/2006 | Guo |
| 2006/0237658 | A1 | 10/2006 | Waluszko |
| 2006/0282137 | A1 | 12/2006 | Nightingale et al. |
| 2007/0053184 | A1 | 3/2007 | Brukilacchio |
| 2007/0053200 | A1 | 3/2007 | Brukilacchio |
| 2007/0058389 | A1 | 3/2007 | Brukilacchio |
| 2007/0064202 | A1 | 3/2007 | Moffat et al. |
| 2007/0086006 | A1 | 4/2007 | Ebersole et al. |
| 2007/0126017 | A1 | 6/2007 | Krames et al. |
| 2007/0211460 | A1 | 9/2007 | Ravkin |
| 2007/0253733 | A1 | 11/2007 | Fey |
| 2007/0262731 | A1* | 11/2007 | Jaffar et al. .................. 315/291 |
| 2007/0279914 | A1 | 12/2007 | Rutherford et al. |
| 2007/0279915 | A1 | 12/2007 | Rutherford et al. |
| 2007/0280622 | A1 | 12/2007 | Rutherford et al. |
| 2007/0281322 | A1 | 12/2007 | Jaffe et al. |
| 2007/0284513 | A1 | 12/2007 | Fan |
| 2007/0297049 | A1 | 12/2007 | Schadwinkel et al. |
| 2008/0079910 | A1 | 4/2008 | Rutherford et al. |
| 2008/0224024 | A1 | 9/2008 | Ashdown |
| 2008/0291446 | A1 | 11/2008 | Smith |
| 2009/0122533 | A1 | 5/2009 | Brukilacchio |
| 2009/0196046 | A1 | 8/2009 | Rutherford et al. |
| 2009/0268461 | A1 | 10/2009 | Deak et al. |
| 2010/0188017 | A1 | 7/2010 | Brukilacchio |

FOREIGN PATENT DOCUMENTS

| | | |
|---|---|---|
| GB | 0943756 | 12/1963 |
| JP | 2005-195485 | 7/2005 |
| JP | 2005-243973 | 9/2005 |
| JP | 2006-049814 | 2/2006 |
| JP | 2007-133435 | 5/2007 |
| JP | 2008139796 A * | 6/2008 |
| KR | 10-2006-0055934 | 5/2006 |
| WO | WO 02/080577 | 10/2002 |
| WO | WO 2004/114053 | 12/2004 |
| WO | WO 2006/067885 | 6/2006 |
| WO | WO 2006/120586 | 11/2006 |

OTHER PUBLICATIONS

Morgan, C. G., et al., << New Approaches to Lifetime-Resolved Luminescence Imaging, Journal of Fluorescence, vol. 7, No. 1, 1997, pp. 65-73.

International Search Report dated Jun. 19, 2012 for Application No. PCT/US2011/063030, 11 pages.

International Search Report dated Dec. 31, 2008, Application No. PCT/US2008/072394, 10 pages.

International Search Report for PCT/US2010021843 dated Aug. 19, 2010, 9 pages.

Extended European Search Report for PCT/US2008072394 dated Oct. 7, 2011, 9 pages.

Mauch, R.H., et al., "Optical Behaviour of Electroluminescent Devices," Springer Proceedings in Physics, vol. 38, Electroluminescence, © Springer-Verlag Berlin, Heidelberg, pp. 291-295 (1989).

Vlasenko, N.A., et al., "Interference of Luminescent Emission from an Evaporated Phosphor," Opt. Spect., vol. 11, pp. 216-219 (1961).

Vlasenko, N.A., et al., "Investigation of Interference Effects in Thin Electroluminescent ZnS-Mn Films," Opt. Spect., vol. 28, pp. 68-71 (1970).

Poelman, D., et al., "Spectral Shifts in Thin Film Electroluminescent Devices: An Interference Effect," J. Phys. D: Appl. Phys., vol. 25, pp. 1010-1013 (1992).

Tuenge, R.T., "Current Status of Color TFEL Phosphors," Electroluminescence—Proceedings of the Sixth International Workshop on Electroluminescence, El Paso, Tex., pp. 173-177, May 1992.

Plasma Display Manufacturers of the American Display Consortium, "Recommended Research Topics on Plasma Display for the DARPA Sponsored Phosphor Center of Excellence," pp. 1-2, Mar. 24, 1993.

Yamamoto, Y., et al., "Optical Processes in Microcavities," Physics Today, pp. 66-73, Jun. 1993.

E.F. Schubert, E.F., et al., "Giant Enhancement of Luminescence Intensity in Er-doped Si/SiO$_2$ Resonant Cavities," Appl. Phys. Lett. vol. 61, No. 12, pp. 1381-1383, Sep. 21, 1992.

Yokoyama, H., "Physics and Device Applications of Optical Microcavities," Science, vol. 256, pp. 66-70, Apr. 3, 1992.

Haroche, S., et al., "Cavity Quantum Electrodynamics," Scientific American, pp. 54-62, Apr. 1993.

Depp, S.W., et al., "Flat Panel Displays," Scientific American, pp. 90-97, Mar. 1993.

Huo, D.T.C., et al., "Reticulated Single-Crystal Luminescent Screen," J. Electrochem. Soc., vol. 133, No. 7, pp. 1492-1497, Jul. 1986.

Hinds, E.A., "Spectroscopy of Atoms in a Micron-Sized Cavity," (date and periodical title unknown), pp. 18-19.

Whitaker, Jerry C., "Electronic Displays: Technology, Design, and Applications," McGraw-Hill, Inc., pp. 185-192 (1994).

Hecht, Jeff, "Diverse fiberoptic systems require varied sources," Laser Focus World, vol. 36, No. 1, pp. 155-161, Jan. 2000.

Hamberg, I. and Granqvist, C.G., "Evaporated Sn-doped In$_2$O$_3$ films: Basic optical properties and applications to energy-efficient windows," Journal of Applied Physics, vol. 60, No. 11, pp. R123-R159, Dec. 1, 1986.

World Watch, Photonics Spectra, "IR Reflective Coating Boosts Bulb's Output, Recycling of IR Energy Saves Power, Cuts Costs" pp. 40-41, Jan. 1991.

Jenmar Visual Systems, Sunnyvale, CA, 4 pages, no date, but at least as early as Oct. 15, 1998.

DDS™ Rear Projection Screens, LORS™ Reflection Screens, © 1998 Physical Optics Corporation, Torrance, CA, 2 pages.

Schott Glass Technologies, Inc., Schott Total Customer Care, Contrast Enhancement Filters, Duryea, PA, 6 pages, Jan. 1998.

Handbook of Optics, vol. 1—Fundamentals, Techniques, and Design, Second Edition, Chapter 42: Optical Properties of Films and Coatings, J.A. Dobrowolski, pp. 42.3-42.25, McGraw-Hill, Inc., © 1995.

Young, L., "Multilayer Interference Filters with Narrow Stop Bands," Applied Optics, vol. 6, No. 2, pp. 297-312, Feb. 1967.

Hemingway, D.J. and Lissberger, P.H., "Effective Refractive Indices of Metal-Dielectric Interference Filters," Applied Optics, vol. 6, No. 3, pp. 471-476, Mar. 1967.

Holloway, R.J. and Lissberger, P.H., "The Design and Preparation of Induced Transmission Filters," Applied Optics, vol. 8, No. 3, pp. 653-660, Mar. 1969.

Landau, B.V. and Lissberger, P.H., "Theory of Induced-Transmission Filters in Terms of the Concept of Equivalent Layers," Journal of the Optical Society of America, vol. 62, No. 11, pp. 1258-1264, Nov. 1972.

Lissberger, P.H., "Coatings with Induced Transmission," Applied Optics, vol. 20, No. 1, pp. 95-103, Jan. 1, 1981.

Pelletier, E. and MacLeod, H.A., "Interference Filters with Multiple Peaks," Journal of the Optical Society of America, vol. 72, No. 6, pp. 683-687, Jun. 1982.

Da-Lite Screen Company, Inc., www.da-lite.com, 46 pages website downloads as of Oct. 8, 1998.

Stewart Filmscreen Corporation®, www.stewartfilm.com, 34 pages website downloads as of Oct. 8, 1998.

Albrecht, M., et al., "Scintillators and Wavelength Shifters for the Detection of Ionizing Radiation," Astroparticle, Particle and Space Physics, Detectors and Medical Physics Applications, ICATPP-8, M. Barone, et al., Eds, World Scientific, pp. 502-511 (2004).

Flor-Henry, M., et al., "Use of a Highly Sensitive Two-Dimensional Luminescence Imaging System to Monitor Endogenous Bioluminescence in Plant Leaves," BMC Plant Biology, vol. 4, No. 19, Nov. 2004.

* cited by examiner

SYSTEM AND METHOD FOR METERED DOSAGE ILLUMINATION IN A BIOANALYSIS OR OTHER SYSTEM

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF INVENTION

The invention is generally related to light sources, and bioanalytics or bioanalysis, and is particularly related to a system and method for metered dosage illumination in a bioanalysis or other system.

BACKGROUND

Bioanalytics or bioanalysis is the analysis of biological samples. Bioanalysis systems often use light to excite fluorescence from molecular tags in a sample (referred to herein as fluorescent tags or fluors). Fluors may be exogenous, as in the case of fluorescently labeled immunochemical tags that recognize subcellular structure and bind to impose fluorescent labeling; or endogenous, as in the case of genetically modified cells in which fluorescent proteins for example are expressed in order to impart specific fluorescent signals within a living cell. Particularly in fields such as fluorescence imaging, gene expression analysis, various types of sequencing, high resolution fluorescence microscopy, fluorescence life time measurements, and high content screening, it is necessary to be able to measure the amount of fluorescence and compare that amount to other measurements. This means the excitation light flux must generally be measured for each illumination exposure or fluorescence excitation event. To monitor biological events, it is necessary to be able to measure specific biological activity with often sub-millisecond exposure times. Excitation and detection must occur rapidly, such that the illumination must be generally switched on and off within a time period that is at most one-tenth of the duration of the minimum exposure time. Additionally, fluors can be temporarily or permanently photo-bleached, and biological samples can be otherwise damaged by the illumination light—a process known as phototoxicity. In order to minimize perturbation of the fluors due to photo-bleaching, and photo-damage to the biological samples, it is generally desired to minimize the light flux or dosage within the constraints of the signal-to-noise (S/N) requirements of that particular bioanalysis system. These are the general areas that embodiments of the invention are intended to address.

SUMMARY

Described herein is a system and method for metered dosage illumination in a bioanalysis or other system. In accordance with an embodiment, an illumination system or subsystem is described that can provide optimized amounts of excitation light within the short exposure times necessary to measure fast biological activity. The amount of light can be precisely measured to provide quantitative results. The light flux can also be precisely controlled to generate only a prescribed minimum amount of light, in order to reduce adverse lighting effects on both fluors and samples. Although the examples herein illustrate the providing of metered dosage illumination in the context of a bioanalysis system, the techniques can be similarly used to provide metered dosage illumination in the context of other types of system.

DETAILED DESCRIPTION

As described above, in the context of bioanalysis, it is often required that an excitation light flux be measured for each illumination exposure or fluorescence excitation event; or that the illumination be switched on and off within an appropriately brief time period; or that the light flux or dosage be minimized within the constraints of the signal-to-noise (S/N) requirements of the particular bioanalysis system.

To address this, described herein is a system and method for metered dosage illumination in a bioanalysis or other system. In accordance with an embodiment, an illumination system or subsystem is described that can provide optimized amounts of excitation light within the short exposure times necessary to measure fast biological activity. The amount of light can be precisely measured to provide quantitative results. The light flux can also be precisely controlled to generate only a prescribed minimum amount of light, in order to reduce adverse lighting effects on both fluors and samples.

Figure 1:
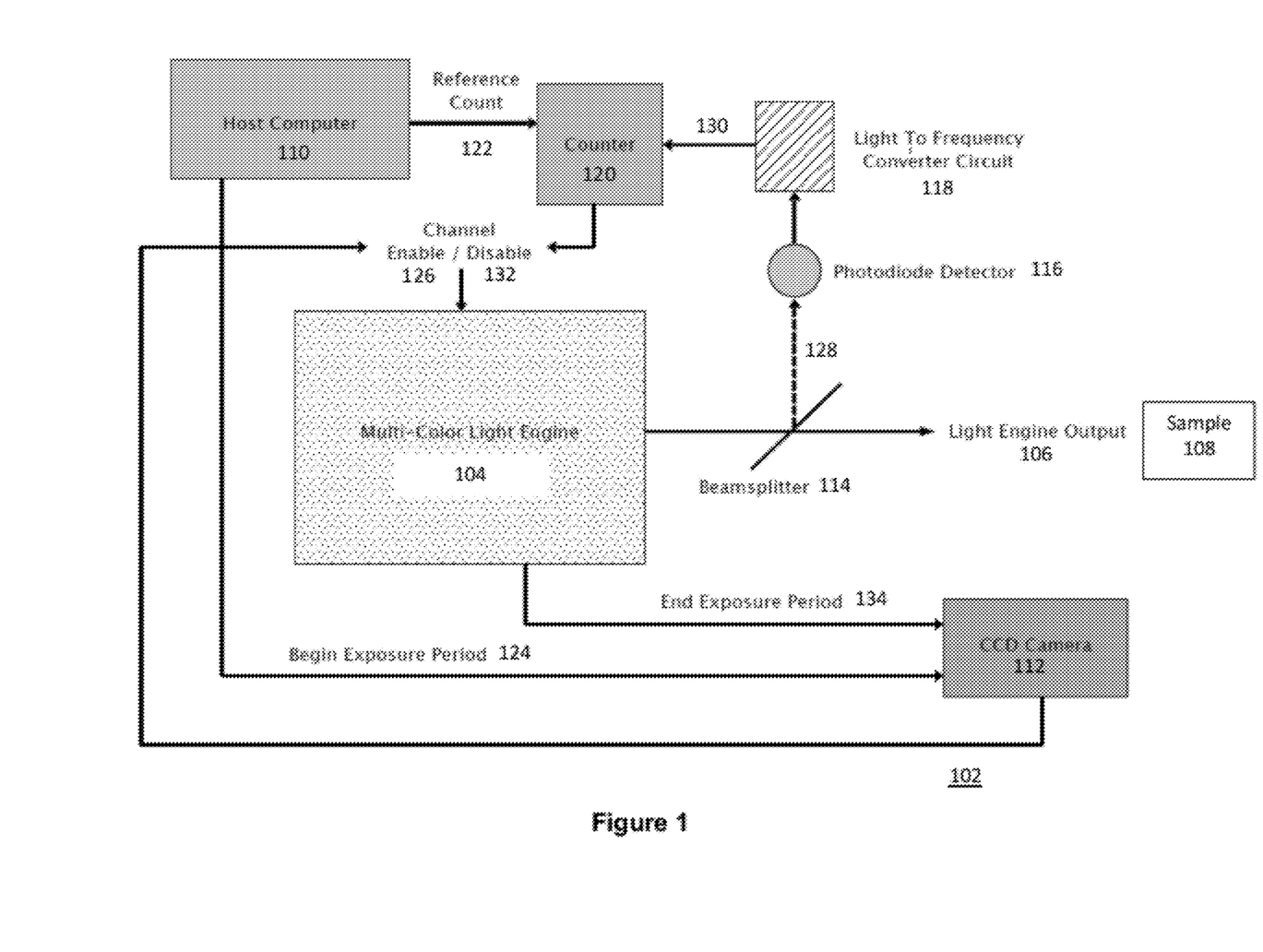
FIG. 1 illustrates a system for metered dosage illumination, in accordance with an embodiment.

FIG. 1 illustrates a system for metered dosage illumination, in accordance with an embodiment. As shown in FIG. 1, in accordance with an embodiment, the system 102 comprises a multi-color light engine 104 that can provide a plurality of different colors of light as a light output 106, to excite various fluorescent markers in a sample 108. An example of such a light engine can be the SPECTRA series of light engines supplied by Lumencor, Inc.

A host computer 110 generates an analysis protocol, including providing a dosage for each of the plurality of colors, and receiving feedback data from a camera 112. In accordance with an embodiment, the dosage can be in the form of a reference count that represents the amount of light flux per exposure period for each color provided by the light engine.

The camera is configured to detect fluorescence from the sample.

A beamsplitter 114 directs a portion of the light engine output, from the light engine, to a photodiode detector 116. A light-to-frequency converter 118 converts the detector output to a pulse train 130, the frequency of which is proportional to the light flux. A microprocessor-based counter 120 counts the pulse train, for each color, and compares the ongoing count to the reference count or preset dosage for each color.

Depending on the particular implementation, the above components can be provided as part of a complete system; or alternatively some or all of the above components can be provided as part of an illumination subsystem. For example, in accordance with an embodiment, the multi-color light engine, beamsplitter, photodiode detector, light-to-frequency converter, and microprocessor-based counter components can be provided as an illumination subsystem intended for use with a separately-provided host computer and camera.

In accordance with an embodiment, during operation of the system, the host computer downloads a reference count 122 for each color to the microprocessor-based counter. For each exposure period, the computer triggers the camera to begin an exposure period 124. The camera then sends an enable message or otherwise enables 126 the light engine, to turn on the appropriate color, and begins integrating the fluorescence. A portion of the light engine output 128, as directed by the beamsplitter, is monitored by the photodiode detector. The detector's output is converted to the pulse train that is then counted by the counter. When the counter reaches the reference count, it disables 132 the color channel currently on or provided by the light engine. Simultaneously, another trigger 134 is sent to the camera, ending the current exposure period.

The above approach avoids the latency inherent in any non-real-time operating systems. In accordance with an embodiment, additional circuitry can be provided to determine which color should be activated, and eliminate any delay inherent in the light engine turning on a color channel. An alternative approach is for the computer to turn on each color directly in conjunction with starting the camera's exposure period. In yet other embodiments, the procedure described above can be modified to suit the particular needs of the system (such as its use in quantitative analyses, or temporally fast analyses, as described below).

Figure 2:
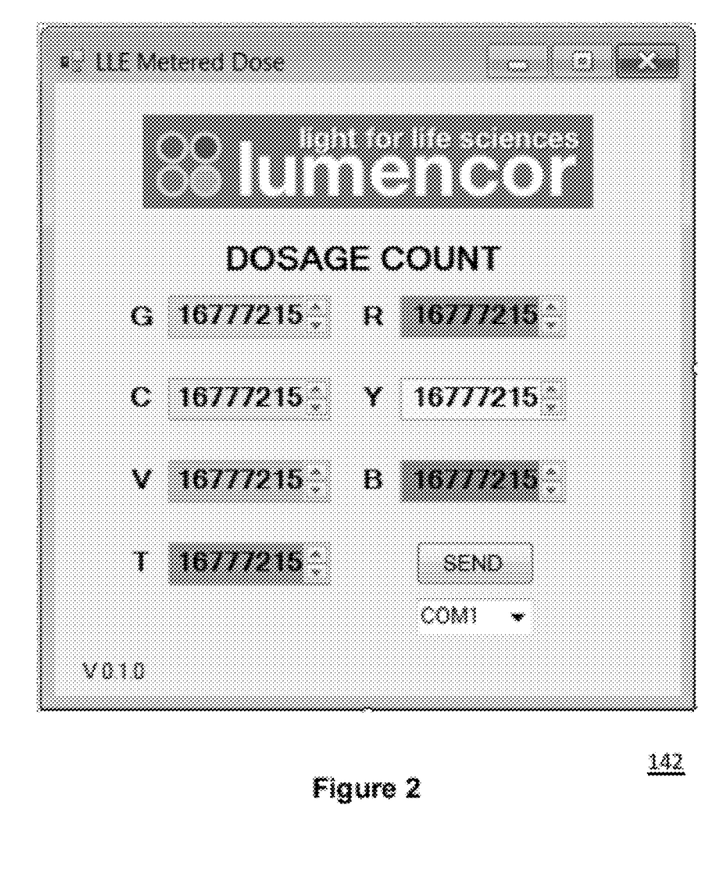
FIG. 2 illustrates an example of a graphical user interface (GUI), for use with a system for metered dosage illumination, in accordance with an embodiment.

FIG. 2 illustrates an example of a graphical user interface (GUI) 142, for use with a system for metered dosage illumination, in accordance with an embodiment. As shown in the example of FIG. 2, the GUI allows an operator to set and to monitor dosage counts in each of the plurality of colors that can be provided by the light engine.

Figure 3:
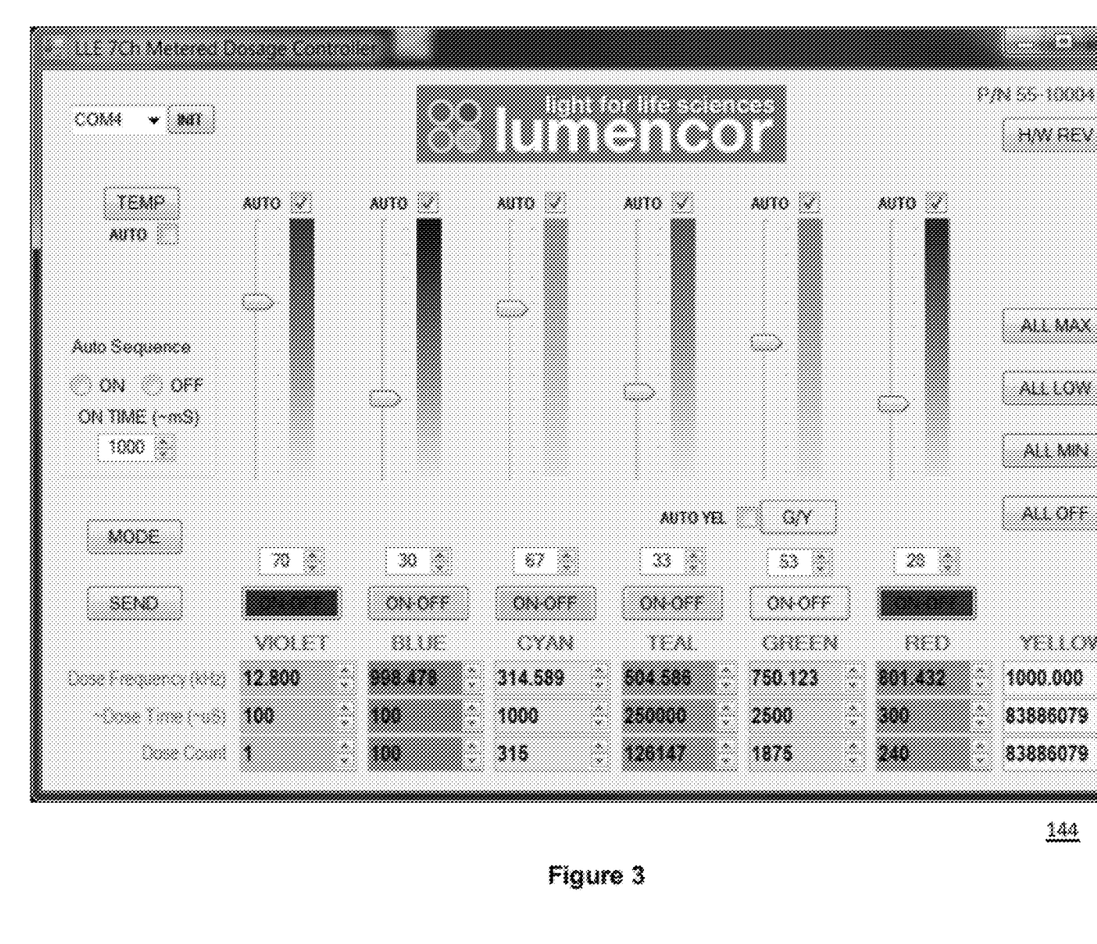
FIG. 3 illustrates an example of an alternative graphical user interface (GUI), for use with a system for metered dosage illumination, in accordance with an embodiment.

FIG. 3 illustrates an example of an alternative graphical user interface (GUI) 144, for use with a system for metered dosage illumination, in accordance with an embodiment. In the example shown in FIG. 3, the GUI controls power levels and exposure times. For each color channel, the operator can enter the relative power levels, maximum dosage frequency and approximate exposure period. In accordance with an embodiment, the system, or software therein, calculates the required dosage or reference count by multiplying the frequency by the desired exposure time. The exposure time is approximate, since the intensity can change resulting in shorter or longer exposure periods, but still yielding the same metered dosage for each period. If the power level is reduced (for example, by half) the dosimeter frequency is similarly reduced by half assuming a linear response. For the same exposure period the calculated dosage is reduced by half.

Quantitative Analysis

In accordance with an embodiment of particular use in quantitivate analysis, the system can comprise a collection of color channels, wherein each color channel is used to provide the specific wavelength band needed to excite a specific fluorescence molecule as defined by the fluorescence absorption of the tag. In accordance with an embodiment, each color channel can comprise a solid state light source (e.g. an LED, laser, light pipe or other light source), a single band pass filter, and an electronic circuit to power the light source. Within the system, the channels can be combined using, e.g. dichroic mirrors, so that the light from each source travels the same optical path, which is required, e.g. in epifluorescence measurements.

In accordance with an embodiment, the control circuitry can use a photodiode to measure the excitation light flux from each channel during each exposure period. An example of such a photodiode can be the TAOS light-to-frequency converter (part number TSL230RD), which can be used to quantify the light flux or dosage for each illumination pulse. The converter circuit generates pulses at a rate that is proportional to the light flux. Counting the pulses yields a measure of the dosage during each exposure time. Since dosage measurements can be made for each color channel independently, the user can optimize the amount of light, using a GUI such as that described above, to irradiate any given fluor uniquely. This allows for differences in efficiencies of all the processes involved in fluorescent signal generation to be taken into account for each color channel, (e.g. efficiency of light generation, fluorescence generation, or various differences in biological sample condition and fluor concentration).

In accordance with an embodiment, quantitative fluorescent measurements can be obtained ratiometrically by measuring the fluorescent signal, and dividing that signal by the dosage. In this manner, the fluorescent measurements can be normalized and rendered independent of the illumination intensity. This approach can be further automated by using dosage measurements to control the timing of the illumination and detection events. For example in accordance with an embodiment, a desired dosage count for each color channel can be entered into a reference counter. During a measurement, the control electronics monitor the dosage and gate off the excitation source for each color when the dosage count equals the amount in the reference counter. Light is metered independently of the exposure time period, rather as a function of the total light delivery prescribed by the reference counter. The precise dosage is delivered during each exposure, leading to quantitation as precise as the light flux measurement.

In this way, quantitative analysis can be performed using metered dosage with or without constant exposure times. In the former case, the light flux is maintained at the same level, and the flux is delivered within the exposure period. After the metered light dosage has been delivered, the excitation light is gated off leaving a time period when the camera can still detect fluorescent signals. In the latter case, the light flux is held constant, and the exposure time will vary as the intensity fluctuates.

In accordance with an embodiment, a range of light levels can be monitored and measured using conventional counters and logic circuitry. In some instances, the dosage levels may be so small as to generate insufficient statistical counts or too large and can overflow the counters. In these instances, a programmable gain can be used to dynamically adjust the count rate from the dosimeter circuitry.

Temporally Fast Analysis

In accordance with an embodiment of particular use in temporally fast analysis, the sources and circuitry can be implemented for fast switching, as is common with LEDs, lasers and light pipes. For example, in accordance with these embodiments, all switching can be performed electronically, with no mechanical motion. This allows modulation in the range of 10 ns to 1 ms to be readily achieved. In addition, significant speed increases can be achieved by directly connecting the camera and the illumination subsystem. In accordance with this embodiment, the host computer can trigger the camera to begin the analysis. The camera in turn can send a trigger to the illumination subsystem to turn on the excitation light. When the dosage count equals the reference count, the light is gated off, and a signal is sent to the camera to end the exposure. This configuration eliminates the variability in timing associated with non-real-time operating systems.

The illumination subsystem can also be used as a direct connection to drive the camera to activate or advance. Color channels can be programmed, e.g. via a ring buffer, to engage camera operation uniquely for each fluor of interest, each excitation source in a preprogrammed series of exposures of the various color channels. The timing of such camera and/or illuminator pulses can be optimized to interrogate specialized fluor characteristics, such as for fluorophor lifetime measurements, photoactivation and photolysis measurements as examples.

Photo-Bleaching and Phototoxicity

In accordance with another embodiment, the ability to precisely meter the light dosage and precisely turn on and off the illumination can minimize overall the exposure of the biological sample to the illuminator's excitation light. In so doing, photo-bleaching and phototoxicity effects are reduced, sample viability for live cell analyses is prolonged, and artifacts imposed by the lighting on the measurement are reduced. The combined benefit of such dosage optimization is enhanced accuracy and longer duration quantitative fluorescent analyses.

Modulation Techniques

Figure 4:
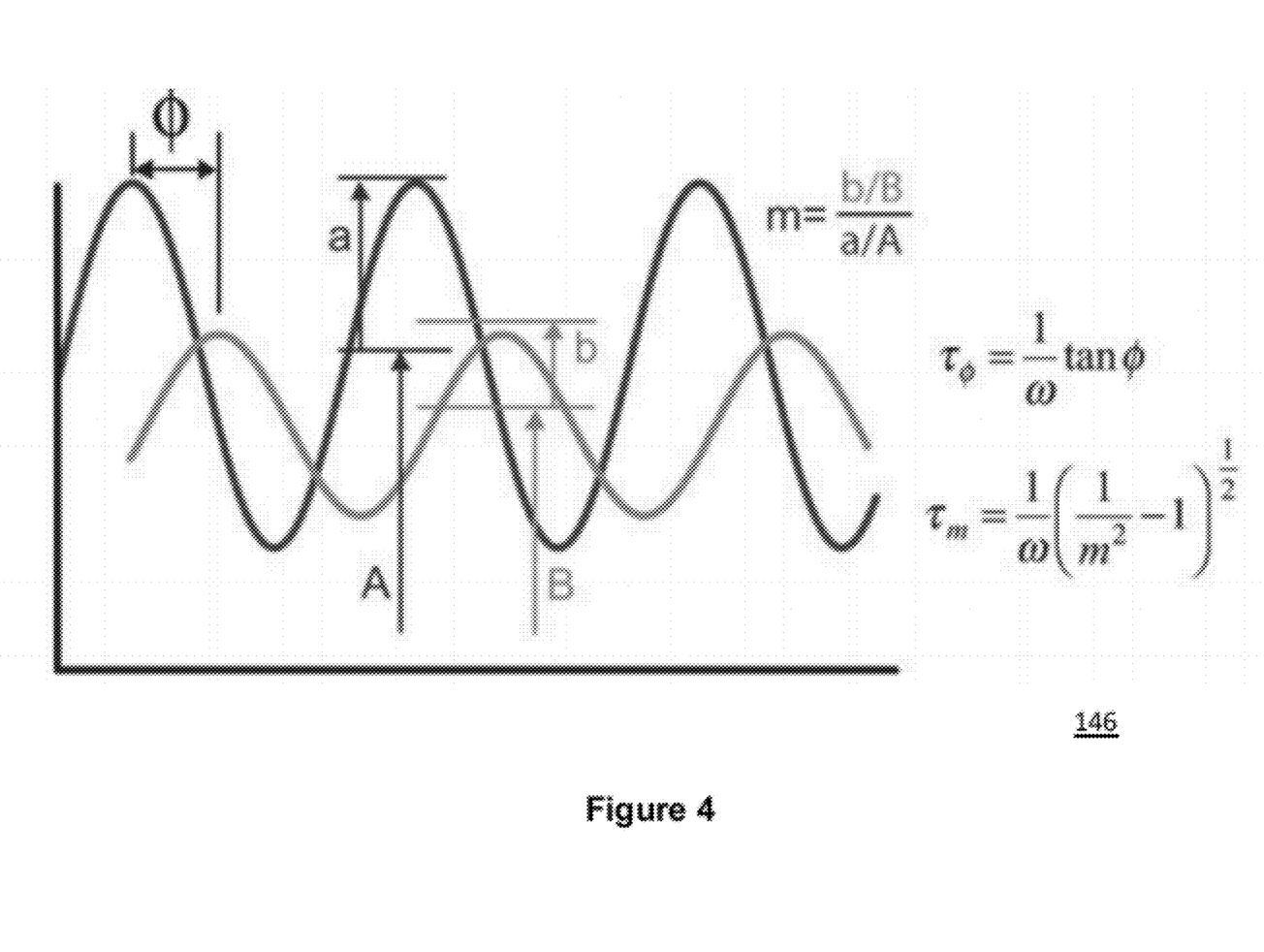
FIG. 4 illustrates an example of a fluorescence lifetime imaging (FLIM) technique, in accordance with an embodiment.

As described above, in accordance with an embodiment, a metered dosage technique can be used to obtain pulse-to-pulse repeatability and increase dynamic range. This technique involves gating the light on and off for the required dosage during each camera exposure period. Other modulation techniques can be used. For example, a modulation technique commonly employed is fluorescence lifetime imaging (FLIM), wherein the illumination is modulated, and the fluorescence lifetime is determined by the phase shift and modulation depth of the fluorescence signal relative to the illumination signal. FIG. 4 illustrates an example of fluorescence lifetime imaging (FLIM) technique 146, in accordance with an embodiment, which is also described at http://www.thorlabs.com/NewGroupPage9.cfm?ObjectGroup_ID=3459; http://en.wikipedia.org/wiki/FLIM; and http://www.lambert-instruments.com/technology_details/1_english/4_technologies/1_flim,_fluorescence_lifetime_imaging_microscopy/7_measurement_methods_flim; http://www.olympusconfocal.com/applications/flimintro.html and http://vvww.microscopyu.com/articles/fluorescence/fret/fretintro.html (Förster Resonance Energy Transfer (FRET) Microscopy), each of which are herein incorporated by reference.

Analog Measurement Techniques

Figure 5:
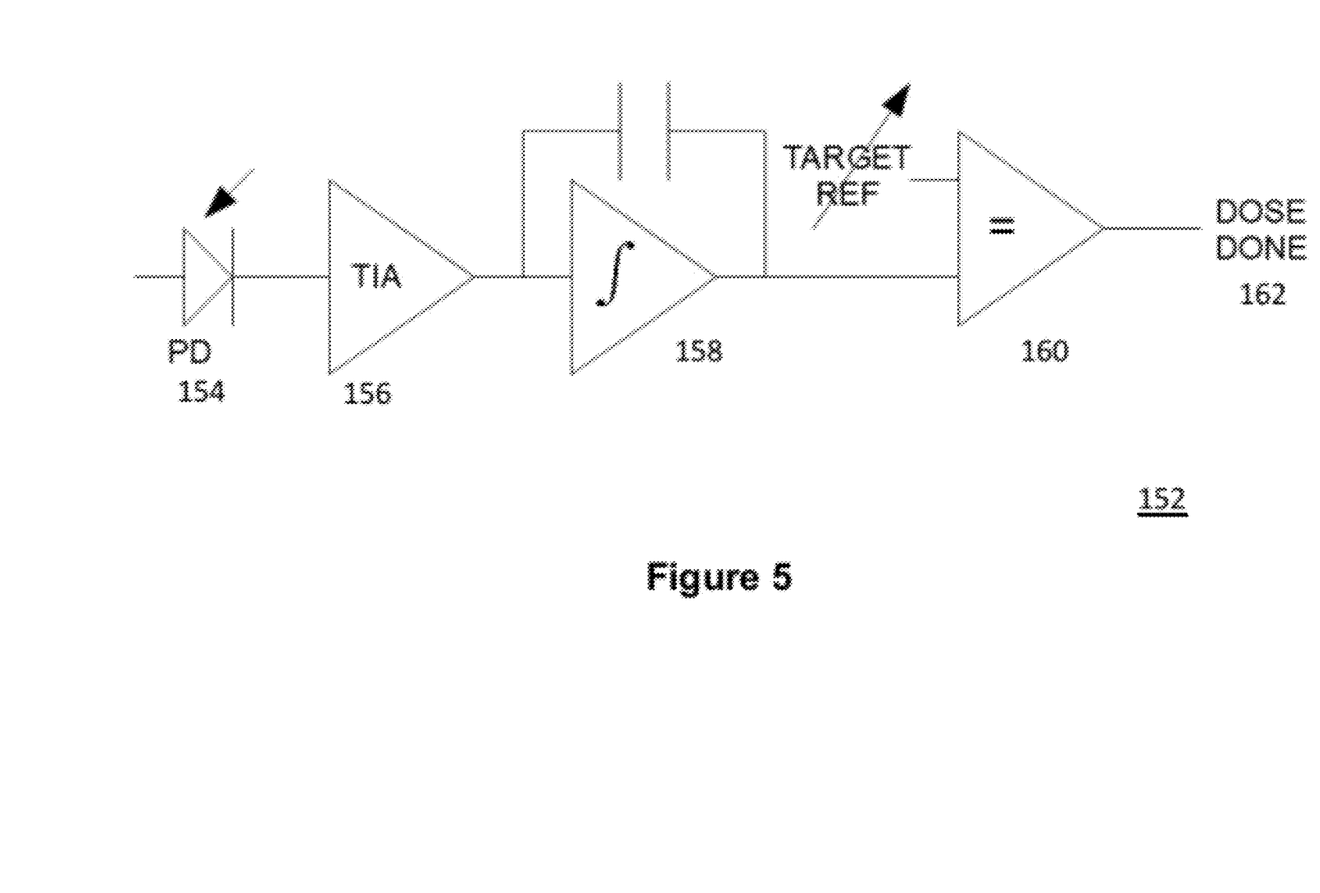
FIG. 5 illustrates an embodiment of an analog measurement of dosage, in accordance with an embodiment.

As described above, in accordance with an embodiment, a host computer can be used to generate an analysis protocol, including providing a dosage for each of the plurality of colors, and receiving feedback data from a camera, while a microprocessor-based counter counts the pulse train, and compares the ongoing count to the reference count or preset dosage for each color. in accordance with other embodiments, alternative measurement techniques, such as analog measurement techniques can be used. FIG. 5 illustrates an embodiment 152 which provides an analog measurement of dosage, in accordance with an embodiment. As shown in FIG. 5, the current output of a photodiode (PD) 154 can be fed to a transimpedance amplifier (TIA) 156, and converted to a voltage. This voltage signal can be integrated by the integrator opamp (∫) 158. The comparator (=) 160 compares the integrator output to a target reference level equal to the desired dosage. When the two values are the same, the comparator can generate a signal 162, turning off the light engine.

The present invention may be conveniently implemented using one or more conventional general purpose or specialized digital computers or microprocessors programmed according to the teachings of the present disclosure. Appropriate software coding can readily be prepared by skilled programmers based on the teachings of the present disclosure, as will be apparent to those skilled in the software art.

In some embodiments, the present invention includes a computer program product which is a storage medium (media) having instructions stored thereon/in which can be used to program a computer to perform any of the processes of the present invention. The storage medium can include, but is not limited to, any type of disk including floppy disks, optical discs, DVD, CD-ROMs, microdrive, and magneto-optical disks, ROMs, RAMs, EPROMs, EEPROMs, DRAMs, VRAMs, flash memory devices, magnetic or optical cards, nanosystems (including molecular memory ICs), or any type of media or device suitable for storing instructions and/or data.

The foregoing description of the present invention has been provided for the purposes of illustration and description. It is not intended to be exhaustive or to limit the invention to the precise forms disclosed. In particular, although most of the examples above illustrate the providing of metered dosage illumination in the context of a bioanalysis system, the techniques can be similarly used to provide metered dosage illumination in the context of other types of systems. The embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the following claims and their equivalence.

What is claimed is:

1. A system for providing metered dosage illumination for use in a bioanalysis or other system, comprising:
   a light engine that can provide a plurality of different colors of light as a light output;
   a light detector that can detect an indication of light flux at the light output;
   a light-to-frequency converter that can convert the indication of light flux as detected by the light detector to a pulse train, the frequency of which pulse train is proportional to the light flux;
   a counter that can compare an ongoing count as indicated by the pulse train, to a preset reference count for a particular color; and
   wherein, during operation, the illumination system
      determines a reference count for each color,
      for an exposure period, enables the light engine to turn on a particular color,
      monitors the indication of light flux at the light output, as detected by the light detector and converted to the pulse train counted by the counter, and
      when the counter reaches the reference count, disables the particular color currently provided by the light engine, to select a different color.

2. The system of claim 1, wherein the light detector is a photodetector for measuring fluorescence that gates on the illumination, and is gated off when the light-to-frequency count equals the reference count.

3. The system of claim 1, wherein the system triggers on the light detector for quantitative measurements and gates the detector off when the frequency detector count equals a prescribed amount in the reference counter.

4. The system of claim 1, wherein the system further comprises a camera for measuring fluorescence, wherein the system gates on the illumination and is gated off when the light to frequency detector count equals the reference count.

5. The system of claim 1, wherein the system further comprises a camera for imaging and wherein the system gates the camera off when the frequency detector count equals a prescribed amount in the reference counter.

6. The system of claim 1, wherein the system is used as part of a bioanalysis system.

7. The system of claim 6, wherein the system is used for detection of fluorescent tags or fluors in a biological sample.

8. The system of claim 7, wherein the system is used for one or more of quantitative analyses, or temporally fast analyses, such as fluorescence imaging, gene expression analysis, various types of sequencing, high resolution fluorescence microscopy, fluorescence life time measurements, various forms of Förster Resonance Energy Transfer (FRET) Microscopy and high content screening.

9. A method for providing metered dosage illumination for use in a bioanalysis or other system, comprising the steps of:

providing a light engine that can provide a plurality of different colors of light as a light output;

providing a light detector that can detect an indication of light flux at the light output;

providing a light-to-frequency converter that can convert the indication of light flux as detected by the light detector to a pulse train, the frequency of which pulse train is proportional to the light flux;

providing a counter that can compare an ongoing count as indicated by the pulse train, to a preset reference count for a particular color; and during operation of the illumination system
determining a reference count for each color,
for an exposure period, enabling the light engine to turn on a particular color,
monitoring the indication of light flux at the light output, as detected by the light detector and converted to the pulse train counted by the counter, and
when the counter reaches the reference count, disabling the particular color currently provided by the light engine, to select a different color.

* * * * *